United States Patent
Faber et al.

(10) Patent No.: US 7,373,851 B2
(45) Date of Patent: May 20, 2008

(54) PULSATILE TEST SIMULATOR FOR EVALUATING THE QUALITY OF AN X-RAY IMAGE

(75) Inventors: Alfred Faber, Langensendelbach (DE);
Robert Jorg, Neunkirchen (DE);
Andreas Melber, Mutlangen (DE);
Thorsten Rombach, Tübingen (DE)

(73) Assignee: Siemens Aktiengesellschaft, Munich (DE)

( * ) Notice: Subject to any disclaimer, the term of this patent is extended or adjusted under 35 U.S.C. 154(b) by 211 days.

(21) Appl. No.: 11/193,966

(22) Filed: Jul. 29, 2005

(65) Prior Publication Data
US 2006/0027741 A1 Feb. 9, 2006

(30) Foreign Application Priority Data
Jul. 29, 2004 (DE) .............. 10 2004 036 797

(51) Int. Cl.
*G01M 19/00* (2006.01)
(52) U.S. Cl. ................................ 73/866.4
(58) Field of Classification Search .............. 73/866.4, 73/865.6; 434/268, 272; 623/3.1, 3.16, 623/3.24
See application file for complete search history.

(56) References Cited

U.S. PATENT DOCUMENTS

| | | | |
|---|---|---|---|
| 4,894,013 A * | 1/1990 | Smith et al. ................. | 434/268 |
| 4,898,181 A | 2/1990 | Kessler ........................ | 600/512 |
| 5,394,455 A | 2/1995 | Roeck et al. ................ | 378/98.3 |
| 5,927,951 A | 7/1999 | Tamari ......................... | 417/63 |
| 6,062,866 A | 5/2000 | Prom ........................... | 434/268 |
| 6,193,669 B1 | 2/2001 | Degany et al. .............. | 600/486 |
| 6,490,336 B1 | 12/2002 | Suess et al. .................. | 378/18 |
| 6,843,145 B2 * | 1/2005 | Jaszczak et al. ............. | 73/866.4 |
| 2002/0136440 A1 | 9/2002 | Yim et al. ................... | 382/131 |
| 2003/0097040 A1 | 5/2003 | Clerin et al. ................. | 600/36 |
| 2003/0220557 A1 | 11/2003 | Cleary et al. ................ | 600/409 |
| 2003/0220718 A1 * | 11/2003 | Jaszczak et al. ............. | 700/282 |

FOREIGN PATENT DOCUMENTS

| | | |
|---|---|---|
| DE | 43 33 365 C2 | 8/1996 |
| EP | 0 825 581 A1 | 7/1997 |
| FR | 2581879 A2 * | 11/1986 |
| FR | 2645739 A * | 10/1990 |
| FR | 2708775 A1 * | 2/1995 |
| GB | 2324902 A * | 11/1998 |
| WO | WO 01/95293 | 12/2001 |

* cited by examiner

*Primary Examiner*—Hezron Williams
*Assistant Examiner*—John Fitzgerald
(74) *Attorney, Agent, or Firm*—Schiff Hardin LLP

(57) ABSTRACT

A test simulator for image evaluation of x-ray systems has a flexible test phantom connected by a single connection tube with a single pump that fills and empties the test phantom with a medium. The test phantom thus contracts (as in a real heartbeat) for simulation of systole and subsequently expands for simulation of diastole. Due to the use of only one connection tube and only one pump for control, a simply designed test simulator is obtained since the pump both fills and empties the test phantom.

18 Claims, 1 Drawing Sheet

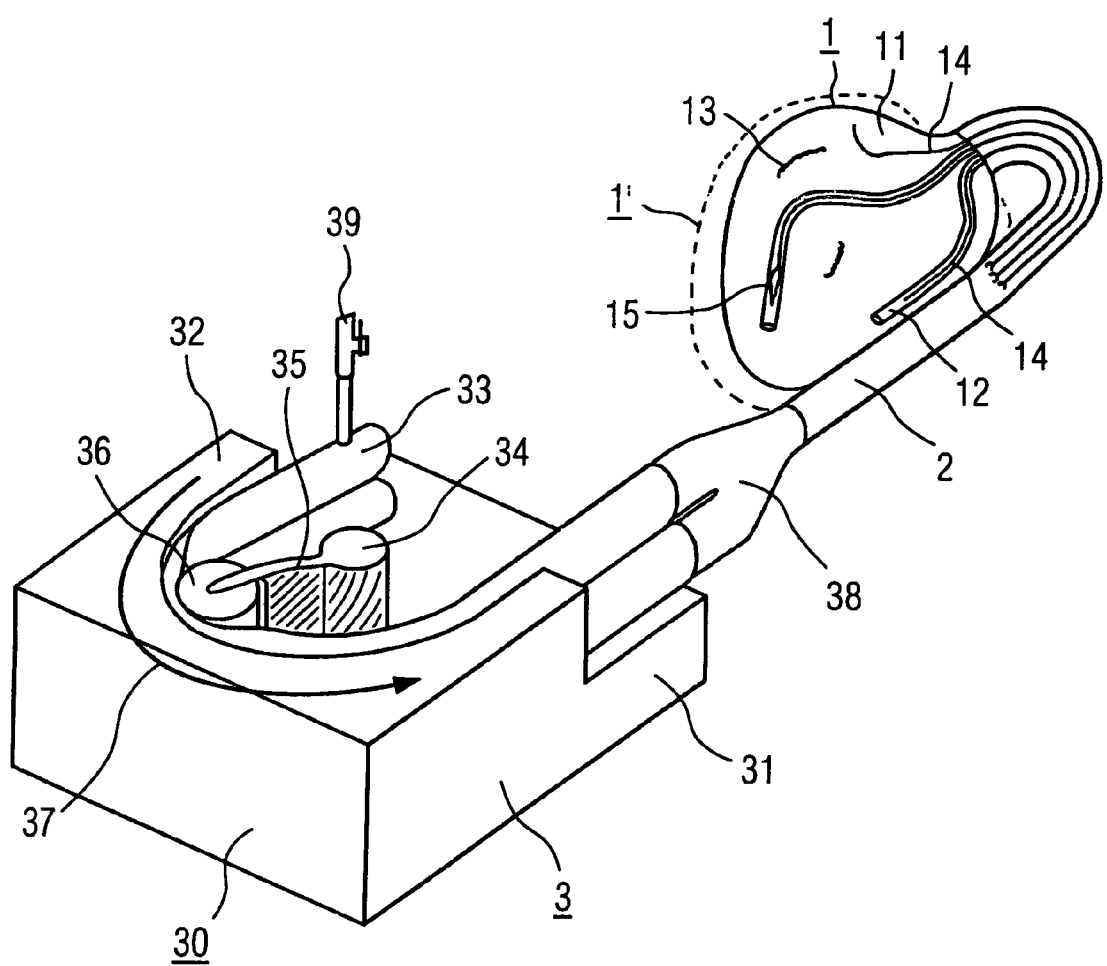

PULSATILE TEST SIMULATOR FOR EVALUATING THE QUALITY OF AN X-RAY IMAGE

BACKGROUND OF THE INVENTION

1. Field of the Invention

The invention concerns a test simulator suitable for use as a pulsatile epicardium simulator for evaluation of the image quality of an x-ray diagnostic device or catheterization equipment.

2. Description of the Prior Art

DE 198 52 325 C2 discloses a test phantom for measurement of slice thicknesses, slice sensitivity profiles and the axial modulation transfer function (MTF) of an x-ray computed tomography apparatus that has a stationary foil or film of a material that significantly attenuates x-ray radiation. Such a test phantom, however, enables only static monitoring, and only from one direction.

For image evaluation in cardio-systems and angiography systems, however, test simulators are necessary that reproduce an anatomical heart movement and enable the evaluation of image tests given clinically relevant angulations of the apparatus.

In EP 0 825 582 A1, a simulation system with a model of an aorta is described that has an inlet and one or more outlets. A fluid is pumped by means of a pump in the model, whereby the outlet is controlled by valves. The model forms a circuit that is relatively complicated to design. An elaborate control of the valves is likewise necessary.

SUMMARY OF THE INVENTION

An object of the invention is to provide a simple test simulator that is suitable for clinically relevant, dynamic image quality evaluation of an x-ray diagnostic device as well as for examination of catheterization equipment, for as many examination conditions in the heart as possible.

The object is inventively achieved by a flexible test phantom connected via a single connection tube with a single pump that fills and empties the test phantom with a fluid medium. The test phantom thus periodically contracts (as with a proper heartbeat) for simulation of the systole and subsequently expands for simulation of the diastole. By the use of only one connection tube and only one pump for control, a simply designed test simulator is obtained since the pump both fills and empties the test phantom.

The flexible test phantom can be formed by an elastic pouch.

Small, flexible tubes that simulate the coronary arteries of a heart can be attached on the surface of the test phantom in an advantageous manner.

In an interventional procedure on the heart with catheterization equipment made visible by x-rays, the test can be made with the catheterization equipment (such as stents, guide wires and/or catheters) attached to the surface of the test phantom. This catheterization equipment can be inventively arranged in the tubes.

It has proven to be advantageous when the catheterization equipment is integrated into the wall of the test phantom. This can already ensue during the manufacturing process. Alternatively, recesses can be provided in the wall of the test phantom during the manufacturing, in which recesses the catheterization equipment can be subsequently installed.

The flexible test phantom can exhibit the shape of the epicardium of the heart.

According to the invention, the medium can be a liquid, for example water. Alternatively, the medium can be a gas.

The pump is a tube pump (for example a peristaltic pump) or a membrane pump.

A simplification of the design is achieved in an embodiment wherein the pump is connected at one side with the connection tube and is sealed on its other side. The pump can be provided on the other, sealed side with a device for filling and venting.

The reservoir for the medium can be enlarged in an embodiment wherein the pump has two tubes disposed on top of one another.

The tubes can be inventively connected with the connection tube on one side thereof via a Y-connector and can be sealed on the other side, where they are provided with a device for filling and venting.

The test simulator achieves a particularly natural simulation in an embodiment wherein the pump is designed such that the volume of the medium for filling/emptying corresponds to the natural blood ejection volume of both heart ventricles.

DESCRIPTION OF THE DRAWING

The single FIGURE is a perspective view of a pulsatile test simulator constructed and operating in accordance with the present invention.

DESCRIPTION OF THE PREFERRED EMBODIMENTS

In the FIGURE, an inventive pulsatile epicardium simulator is shown that is formed by a test phantom that is connected via a connection tube 2 to a tube pump 3 such as a peristaltic pump. The test phantom 1 is formed of an expandable pouch 11 fashioned in the shape of a heart. Small, flexible tubes that simulate the coronary arteries of a heart are fastened on the surface of the pouch 11. Catheterization. equipment (such as stents 13, guide wires 14 or balloon catheters 15) can be integrated into these tubes 12. The catheterization equipment 13 through 15 alternatively can be directly attached to the surface of the pouch 11 or can be incorporated into the wall of the test phantom 1.

Instead of the tube pump 3, a membrane pump can be provided that exhibits a smaller design.

The tube pump 3 has a carrier 30 having a base 31. From three sides of the base 31, sidewalls 32 project forming a U-shape. Two tubes 33 are placed one atop the other on the U-shaped inner surface of the sidewalls 32. A drive axle 34 of a drive motor (not shown) protrudes into the center of the U-shaped sidewalls 32, on which drive axle 34 a roller 36 is attached via a lever 35. This roller 36 presses the tube 33 against the inner surface of the sidewalls 32 so that the medium cannot pass through the pinched (compressed) tubes 33 at this point. The medium contained in the tubes 22 is thus pushed into the test phantom 1 by rotation of this arrangement 34 through 36 in the direction of an arrow 37, such that the test phantom expands to the size 1' indicated by the dashed line. This expansion ensues slowly, corresponding to the rotation speed of the drive motor of the pump 3. When the roller 36 rotates out of the region of the sidewalls 32, a fast contraction of the pouch 11 ensues since the medium can flow unhindered back into the tubes 33 due to the pressure generated by the pouch 11. The speed of the return flow can possibly be regulated by a valve or suitable constructions. The pump action begins again after a further 180° rotation. This event repeats periodically.

Alternatively, for contraction of the test phantom 1 the rotation direction of the drive motor of the pump 3 can be reversed so that the medium is pumped out of the pouch 11.

The tubes 33 are connected with the connection tube 2 at one side via a Y-connection 38. The tubes 33 are sealed on the other side, where they are provided with a device 39 for filling and venting. Additionally, valves can be introduced into the tubes 33 by means of which the flow rate of the medium can be regulated. Instead of two tubes 33, only one tube can be provided, but this must correspond in terms of size with the pump volume (and therewith the natural blood ejection volume) of both heart ventricles. A pump type other than the tube (peristaltic) pump 3 can also be used.

In order to simulate the external movement of the human heart, the elastic synthetic pouch 11 with the shape of the heart tissue epicardium is filled and emptied with a medium via a single connection tube 2 connected to a single pump 3, with the medium being liquid or gaseous. For example, water can be used as a liquid medium. The connection tube 2 thus additionally serves as a reservoir for the medium. The material of the pouch 11 is brought to the size of the heart in diastole by pre-filling with the medium. The volume of the medium for filling/emptying corresponds to the natural blood ejection volume of both heart ventricles. When this volume is additionally conveyed into the pouch 11 and subsequently extracted therefrom again, the pouch 11 expands and contracts and thereby simulates the heart movement during a heartbeat.

For special application in the evaluation of the image quality under x-ray radiation, the coronary arteries are simulated by small, flexible tubes 12 fastened on the surface of the epicardium simulator. Diverse catheterization equipment (such as the stents 13, guide wires 14 and catheter 15, etc.) that must be made visible in an intervention on the heart by x-ray radiation are in turn placed in these tubes 12.

Different heartbeat rates can be set by a variable rotational frequency of the pump 3.

A clinically relevant heart movement can be reproduced by the inventive, pulsatile epicardium simulator. A test evaluation is possible from all angulations.

A realistic water equivalent is achieved when the pouch 11 is filled with water. Due to the dimension of the epicardium simulator, the design is very well adapted for placement at a patient table (bed) of an examination apparatus.

The heart size can be varied in a simple manner by pre-filling the pouch 11 with the medium.

Although modifications and changes may be suggested by those skilled in the art, it is the intention of the inventors to embody within the patent warranted hereon all changes and modifications as reasonably and properly come within the scope of their contribution to the art.

We claim as our invention:

1. A pulsatile test simulator comprising:
   a flexible medical imaging test phantom representing a heart and forming an elastic pouch having an interior;
   a single connection tube connected to said flexible test phantom and communicating with said interior of said pouch;
   a single pump connected to said connection tube that pumps a fluid medium that successively fills and empties said interior of said pouch to cause said test phantom to expand and contract, with filling said interior representing diastole and emptying said interior representing systole.

2. A test simulator as claimed in claim 1 wherein said pump has a pumping volume for said fluid medium corresponding to a natural blood ejection volume of both ventricles of a human heart.

3. A test simulator as claimed in claim 1 comprising a plurality of flexible tubes attached to an exterior surface of said test phantom to simulate coronary arteries of a heart.

4. A test simulator as claimed in claim 1 wherein said fluid medium is a gas.

5. A test simulator as claimed in claim 1 wherein said pump is a membrane pump.

6. A test simulator as claimed in claim 1 wherein said test phantom has a size and shape simulating a cardiac epicardium.

7. A test simulator as claimed in claim 1 wherein said fluid medium is a liquid.

8. A test simulator as claimed in claim 7 wherein said liquid is water.

9. A test simulator as claimed in claim 1 comprising catheterization equipment attached to an exterior surface of the test phantom.

10. A test simulator as claimed in claim 9 comprising a plurality of flexible tubes attached on said exterior surface of said test phantom to simulate coronary arteries of a heart, and wherein said catheterization equipment is disposed in said tubes.

11. A test simulator as claimed in claim 9 wherein said test phantom has a phantom wall comprising said exterior surface, and wherein said catheterization equipment is integrated into said wall.

12. A test simulator as claimed in claim 9 wherein said catheterization equipment is selected from the group consisting of stents, guide wires and catheters.

13. A test simulator as claimed in claim 1 wherein said pump is a tube pump.

14. A test simulator as claimed in claim 13 wherein said tube pump is a peristaltic pump.

15. A test simulator as claimed in claim 13 wherein said pump is a tube pump comprising two tubes disposed one above the other.

16. A test simulator as claimed in claim 15 wherein said tubes have a first end and a second end opposite said first end, and wherein said test simulator comprises a Y-connection connecting said first end of said tubes to said connection tube, and a filling and venting element disposed at said second end of said tubes.

17. A test simulator as claimed in claim 1 wherein said pump is connected at a first side of said pump with said connection tube, and wherein said pump has an opposite pump side that is sealed.

18. A test simulator as claimed in claim 17 comprising a filling and venting element disposed at said opposite pump side.

* * * * *